United States Patent
Liu

(10) Patent No.: US 9,974,514 B2
(45) Date of Patent: *May 22, 2018

(54) SYSTEM AND METHOD FOR CORRECTING FOR IMAGE ARTIFACTS IN X-RAY IMAGE DATA

(71) Applicant: GENERAL ELECTRIC COMPANY, Schenectady, NY (US)

(72) Inventor: James Zhengshe Liu, Salt Lake City, UT (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 606 days.

This patent is subject to a terminal disclaimer.

(21) Appl. No.: 14/512,643

(22) Filed: Oct. 13, 2014

(65) Prior Publication Data

US 2015/0030130 A1     Jan. 29, 2015

Related U.S. Application Data

(63) Continuation of application No. 13/588,832, filed on Aug. 17, 2012, now Pat. No. 8,950,938.

(51) Int. Cl.
*A61B 6/00* (2006.01)
*G06T 5/00* (2006.01)
*A61B 6/04* (2006.01)

(52) U.S. Cl.
CPC ............ *A61B 6/585* (2013.01); *A61B 6/5211* (2013.01); *A61B 6/5258* (2013.01); *G06T 5/009* (2013.01);

(Continued)

(58) Field of Classification Search
CPC .......... A61B 5/72; A61B 5/7207; A61B 6/52; A61B 6/5205; A61B 6/5211;

(Continued)

(56) References Cited

U.S. PATENT DOCUMENTS 7,053,806 B1   5/2006  Rao et al.
7,963,697 B2   6/2011  Liu et al.

(Continued)

OTHER PUBLICATIONS

Kim, Ho Kyung, et al.; "Radiation Effects on the Performance of CMOS Photodiode Array Detectors and the Role of Gain-Offset Corrections," Jun. 2009, IEEE Transactions on Nuclear Science, vol. 56, No. 3, p. 1179.

(Continued)

*Primary Examiner* — Glen Kao
*Assistant Examiner* — Chih-Cheng Kao

(57) ABSTRACT

A computer-implemented method for reducing image artifacts in X-ray image data includes dividing pixels of X-ray image data into a plurality of pixel value regions based on a pixel value of each pixel, wherein each pixel value region has a different range of pixel values. The method also includes generating calibrated X-ray image data for each pixel value region, wherein the respective calibrated X-ray image data for each pixel value region is generated using a different dose of radiation. Further, the method includes calculating a gain slope for each pixel value region based on the calibrated X-ray image data, and calculating a pixel gain correction for the pixels of the X-ray image data based on at least one of the calculated gain slopes.

21 Claims, 7 Drawing Sheets

(52) U.S. Cl.
CPC ........... *A61B 6/0407* (2013.01); *A61B 6/4405* (2013.01); *A61B 6/4441* (2013.01); *A61B 6/4464* (2013.01); *G06T 2207/10116* (2013.01); *G06T 2207/30004* (2013.01)

(58) Field of Classification Search
CPC ....... A61B 6/5258; A61B 8/52; A61B 8/5215; A61B 8/5269; A61B 2576/00; G06T 5/001; G06T 5/006; G06T 5/20; G06T 5/40; G06T 5/50; G06T 7/0002; G06T 7/40; G06T 2200/28; G06T 2207/10116
See application file for complete search history.

(56) References Cited

U.S. PATENT DOCUMENTS

| | | |
|---|---|---|
| 8,008,641 B2 | 8/2011 | Harris et al. |
| 8,950,938 B2* | 2/2015 | Liu .......................... G06T 5/009 |
| | | 378/207 |
| 2009/0129659 A1 | 5/2009 | Deutschmann |
| 2010/0183124 A1 | 7/2010 | Liu et al. |

OTHER PUBLICATIONS

International Search Report and Written Opinion for PCT/US2013/054757, dated Jan. 10, 2014; 10 pages.

\* cited by examiner

SYSTEM AND METHOD FOR CORRECTING FOR IMAGE ARTIFACTS IN X-RAY IMAGE DATA

CROSS-REFERENCE TO RELATED APPLICATION

This application claims priority to and the benefit of U.S. patent application Ser. No. 13/588,832, entitled "SYSTEM AND METHOD FOR CORRECTING FOR IMAGE ARTIFACTS IN X-RAY IMAGE DATA", filed Aug. 17, 2012, which is herein incorporated by reference in its entirety.

BACKGROUND

The subject matter disclosed herein relates to X-ray imaging systems and more particularly to correcting for image artifacts in X-ray image data in X-ray imaging systems.

Digital X-ray imaging systems are becoming increasingly widespread for producing digital data which can be reconstructed into useful radiographic images. In current digital X-ray imaging systems, radiation from a source is directed toward a subject, typically a patient in a medical diagnostic application. A portion of the radiation passes through the patient and impacts a detector. The scintillator of the detector converts the radiation to light photons that are sensed. The detector is divided into a matrix of discrete picture elements or pixels, and encodes output signals based upon the quantity or intensity of the radiation impacting each pixel region, as measured by a receptor. The signals may then be processed to generate an image that may be displayed for review.

The relationship between input intensity of the radiation impacting the detector and detector output may vary between the pixels of the detector. Calibration of the detector can correct for such variations. However, the relationship between intensity of radiation impacting the detector and detector output can be difficult to calibrate across a certain dynamic range of X-ray doses that may be applied to the detector.

BRIEF DESCRIPTION

In one embodiment of the present disclosure, a computer-implemented method for reducing image artifacts in X-ray image data includes dividing pixels of X-ray image data into a plurality of pixel value regions based on a pixel value of each pixel, wherein each pixel value region has a different range of pixel values. The method also includes generating calibrated X-ray image data for each pixel value region, wherein the respective calibrated X-ray image data for each pixel value region is generated using a different dose of radiation. Further, the method includes calculating a gain slope for each pixel value region based on the calibrated X-ray image data, and calculating a pixel gain correction for the pixels of the X-ray image data based on at least one of the calculated gain slopes.

In another embodiment of the present disclosure, one or more non-transitory computer-readable media encoding one or more processor-executable routines are provided. The routines, when executed by a processor, cause acts to be performed, including dividing pixels of X-ray image data into a plurality of pixel value regions based on a pixel value of each pixel, wherein each pixel value region has a different range of pixel values. The acts performed by the routines also include generating calibrated X-ray image data for each pixel value region, wherein the respective calibrated X-ray image data for each pixel value region is generated using a different dose of radiation. Further, the routines perform acts including calculating a gain slope for each pixel value region based on the calibrated X-ray image data and calculating a pixel gain correction for the pixels of the X-ray image data based on at least one of the calculated gain slopes.

In a further embodiment of the present disclosure, an imaging system includes a radiation source, a digital X-ray detector configured to generate X-ray image data, and control circuitry configured to apply a gain correction to the X-ray image data via a plurality of slope maps. The processing circuitry is configured to generate the slope maps by executing code to perform the act of dividing pixels of X-ray image data into a plurality of pixel value regions based on a pixel value of each pixel, wherein each pixel value region has a different range of pixel values. The executed code also performs the acts of generating calibrated X-ray image data for each pixel value region, wherein the respective calibrated X-ray image data for each pixel value region is generated using a different dose of radiation, and calculating a gain slope for each pixel value region based on the calibrated X-ray image data.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Present embodiments are directed to systems and methods for correcting for image artifacts in X-ray image data. Such image artifacts may be a result of a nonlinear relationship between the dose of radiation applied to an X-ray detector and the pixel values output by the detector elements. The X-ray imaging system is designed to divide X-ray image data output by the detector elements into multiple pixel value regions. The pixel value regions have different ranges of pixel values separated by pixel value boundaries. Once divided into multiple pixel value regions, a dose of radiation may be applied to the detector for calibration of each pixel value region. This enables the detector to generate calibrated X-ray image data for each pixel value region in response to the applied X-ray dose. A processor of the X-ray system may calculate a linear gain slope for each of the pixel value regions from average values of the calibrated X-ray image data for each region. Using these gain slopes, the processor may determine a gain correction value to apply to each detector element based on the pixel output of the detector and the pixel value region in which the pixel output is located. In this way, the X-ray system performs a simple correction of X-ray image data based on linear slope maps developed from calibrating the detector across different ranges of pixel values.

Figure 1:
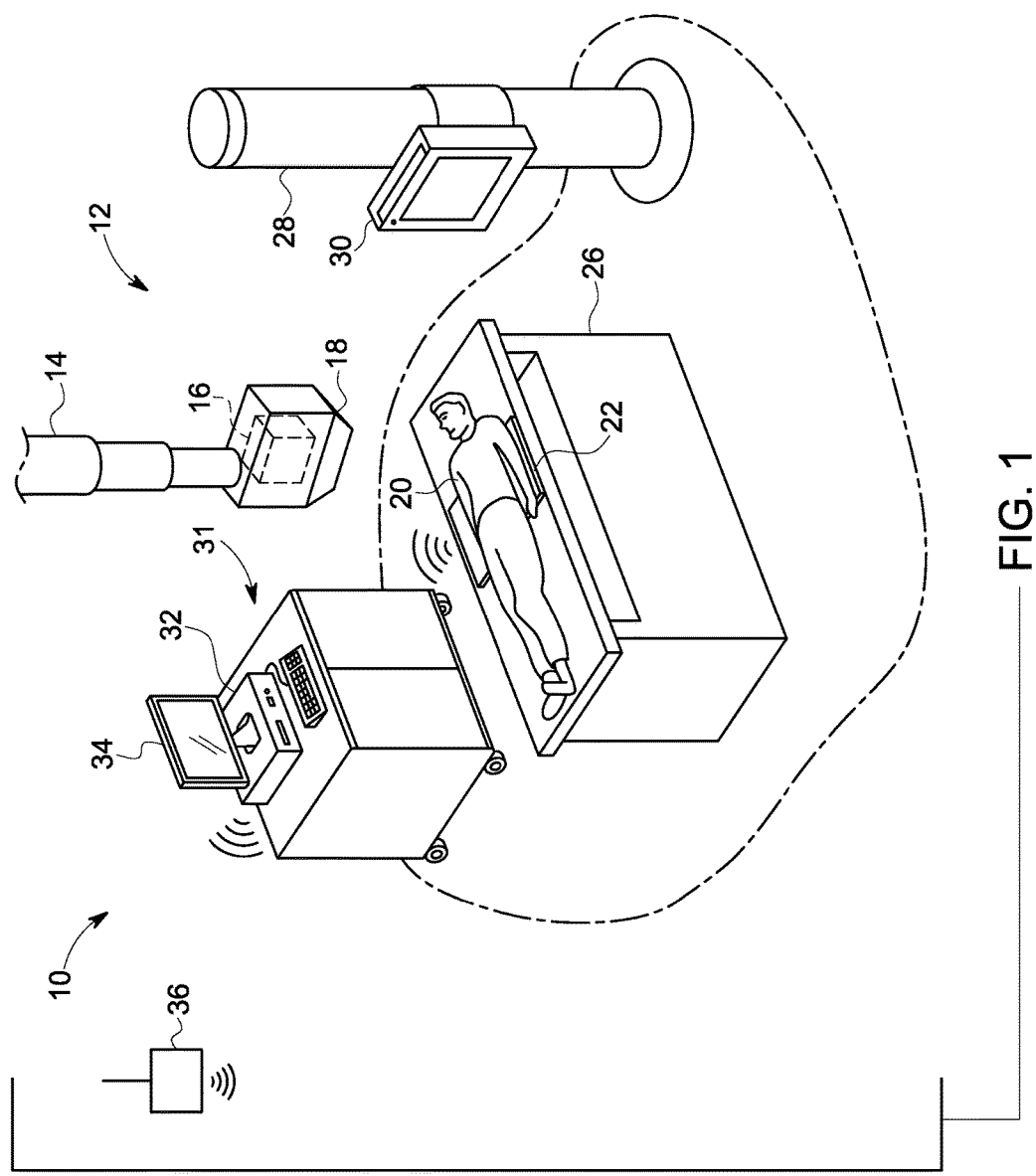
FIG. 1 is perspective view of an embodiment of a fixed X-ray system, equipped in accordance with aspects of the present disclosure.

Referring generally to FIG. 1, an imaging system, in particular an X-ray system is represented and referenced generally by reference numeral 10. In the illustrated embodiment, the X-ray system 10 is a digital X-ray system. The X-ray system 10 is designed both to acquire original image data and to process the image data for display in accordance with present techniques. The X-ray system 10 may be a radiographic imaging system used to collect a standalone image, or a fluoroscopic imaging system used to collect multiple frames of real-time image data. In the embodiment illustrated in FIG. 1, the X-ray system 10 includes an imager system 12. The imager system 12 includes an overhead tube support arm 14 for positioning a radiation source 16, such as an X-ray tube, and a collimator 18 with respect to a patient 20 and a portable digital X-ray detector 22. In one embodiment, the imager system 12 may be used in consort with one or both of a patient table 26 and a wall stand 28 to facilitate image acquisition. Particularly, the table 26 and the wall stand 28 may be configured to receive the detector 22. For instance, the detector 22 may be placed on an upper, lower, or intermediate surface of the table 26, and the patient 20 (more specifically, an anatomy of interest of the patient 20) may be positioned on the table 26 between the detector 22 and the radiation source 16. The wall stand 28 may include a receiving structure 30 also adapted to receive the detector 22, and the patient 20 may be positioned adjacent the wall stand 28 to enable the image data to be acquired via the detector 22. The receiving structure 30 may be moved vertically along the wall stand 28.

Also depicted in FIG. 1, the imager system 12 includes a systems cabinet 31 that includes a workstation 32 and display 34. In one embodiment, the workstation 32 may include or provide the functionality of the imager system 12 such that a user, by interacting with the workstation 32, may control operation of the source 16 and detector 22. The detector 22 may be in communication with the workstation 32 as described below. The workstation 32 may house systems electronic circuitry that acquires image data from the detector 22 and that, where properly equipped (e.g., when the workstation 32 includes processing circuitry), may process the data to form desired images. In addition, the systems electronic circuitry both provides and controls power to the X-ray source 16. The workstation 32 may include buttons, switches, or the like to facilitate operation of the X-ray source 16 and detector 22. In one embodiment, the workstation 32 may be configured to function as a server of instructions and/or content on a network 36 of the medical facility, such as a hospital information system (HIS), a radiology information system (RIS), and/or picture archiving communication system (PACS). In certain embodiments, the workstation 32 and/or detector 22 may wirelessly communicate with the network 36.

In present embodiments, the detector 22 includes circuitry for processing the image data acquired through the detector 22 before communicating the processed image data to the workstation 32. The detector 22 may have a nonlinear relationship between the dose of X-ray radiation received by the detector 22 and the signals output by the pixels of the detector 22. To account for this nonlinearity, the processing circuitry may apply a gain correction to the signals before they are communicated to the workstation 32 for storing or viewing. The detector 22 may be calibrated at different doses of radiation, and the processing circuitry may execute steps to calculate a pixel gain correction for each receptor outputting pixel values within a certain range. That is, the detector 22 may be calibrated separately for each pixel value range before images are produced by the X-ray system 10. In other embodiments, such calibration and processing of the image data acquired through the detector 22 may be performed via processing circuitry in the workstation 32 after the image data is communicated from the detector 22 to the workstation 32. In certain embodiments, the detector 22 may be used in a radiographic X-ray imaging system, while in other embodiments the detector 22 may be used in a fluoroscopic X-ray imaging system. In either context, the presently described calibration and image processing techniques may be applied to the X-ray system 10 for correcting nonlinearity in the detector 22.

In one embodiment, the imager system 12 may be a stationary system disposed in a fixed X-ray imaging room, such as that generally depicted in and described above with respect to FIG. 1. It will be appreciated, however, that the presently disclosed techniques may also be employed with other imaging systems, including mobile X-ray units and systems, in other embodiments.

Figure 2:
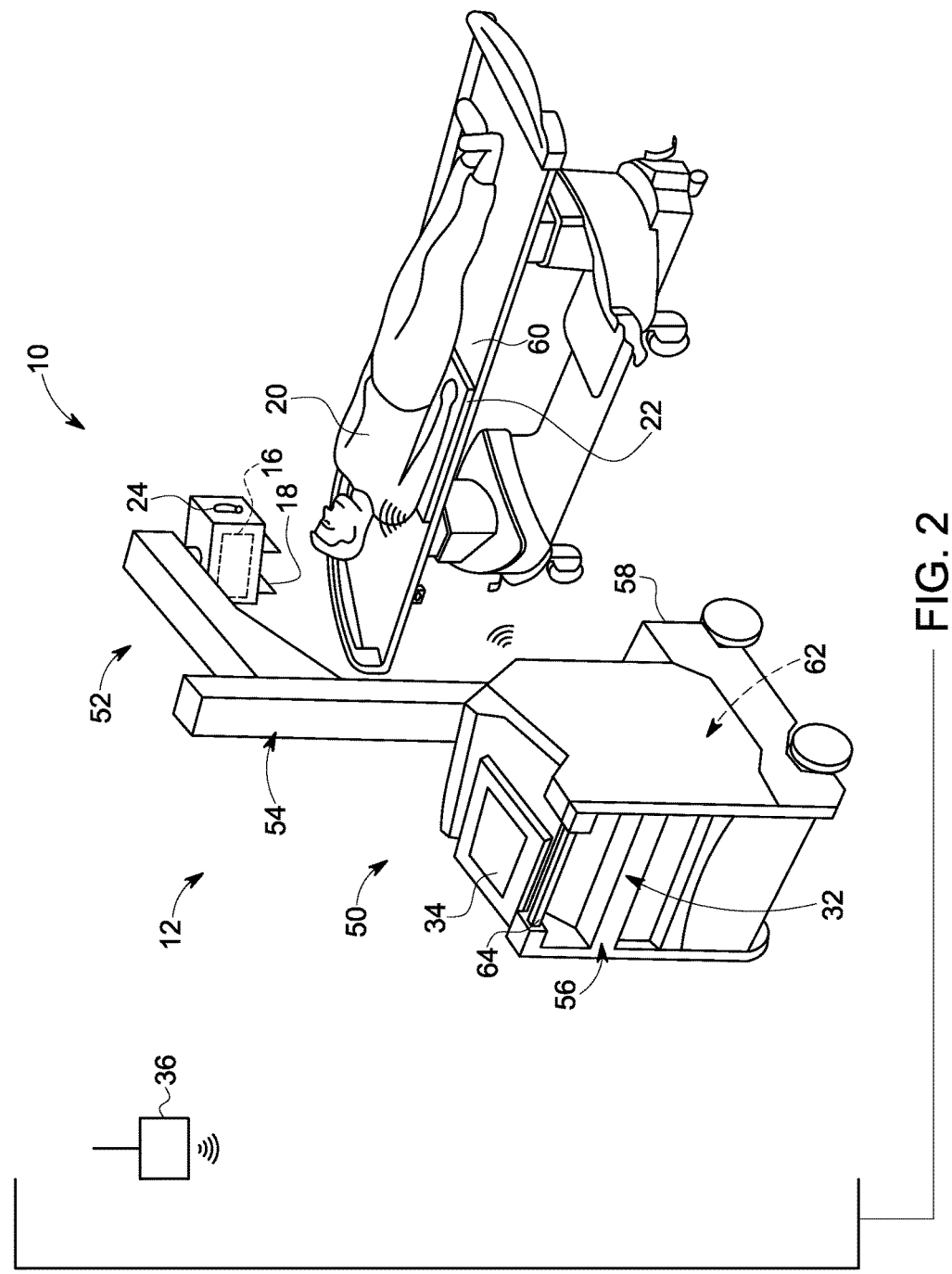
FIG. 2 is a perspective view of an embodiment of a mobile X-ray system.

For instance, as illustrated in the medical imaging system 10 (e.g., X-ray system) of FIG. 2, the imager system 12 may be moved to a patient recovery room, an emergency room, a surgical room, or any other space to enable imaging of the patient 20 without requiring transport of the patient 20 to a dedicated (i.e., fixed) X-ray imaging room. The X-ray system 10 includes a mobile imager or mobile X-ray base station 50 and a portable digital X-ray detector 22. As above, the illustrated X-ray system 10 is a digital X-ray system. In one embodiment, a support arm 52 may be vertically moved along a support column 54 to facilitate positioning of the radiation source 16 and collimator 18 with respect to the patient 20. Further, one or both of the support arm 52 and support column 54 may also be configured to allow rotation of the radiation source 16 about an axis. In addition, the X-ray base station 50 has a wheeled base 58 for movement of the station 50.

The patient 20 may be located on a bed 60 (or gurney, table or any other support) between the X-ray source 24 and the detector 22 and subjected to X-rays that pass through the patient 20. During an imaging sequence using the digital X-ray system 10, the detector 22 receives X-rays that pass through the patient 20 and transmits imaging data to a base unit 56. The detector 22 is in wireless communication with the base unit 56. The base unit 56 houses systems electronic circuitry 62 that acquires image data from the detector 22 and that, where properly equipped, may process the data to form desired images. In addition, the systems electronic circuitry 62 both provides and controls power to the X-ray source 16 and the wheeled base 58. The base unit 56 also has the operator workstation 32 and display 34 that enables the user to operate the X-ray system 10. The operator workstation 32 may include buttons, switches, or the like to facilitate operation of the X-ray source 16 and detector 22. In one embodiment, the workstation 32 may be configured to function as a server of instructions and/or content on the network 36 of the medical facility, such as HIS, RIS, and/or PACS. In certain embodiments, the workstation 32 and/or detector 22 may wirelessly communicate with the network 36.

Similar to the X-ray system 10 in FIG. 1, components of the imager system 12 (e.g., base unit 56) and the detector 22 are configured to perform a correction of the X-ray image data based on a multi-part calibration. That is, multiple calibration images are obtained by the detector 22 to determine receptor outputs at different radiation doses. From the calibration images, a number of slope maps may be generated, each slope map corresponding with a different range of pixel output values. A gain correction for X-ray image data may then be determined based on one or more of the slope maps generated through this calibration, depending on the pixel value region in which a pixel of the X-ray image data is located. The generated slope maps may be utilized to provide corrected X-ray image data in a variety of mobile X-ray systems 10, including radiographic imaging systems and fluoroscopic imaging systems.

Figure 3:
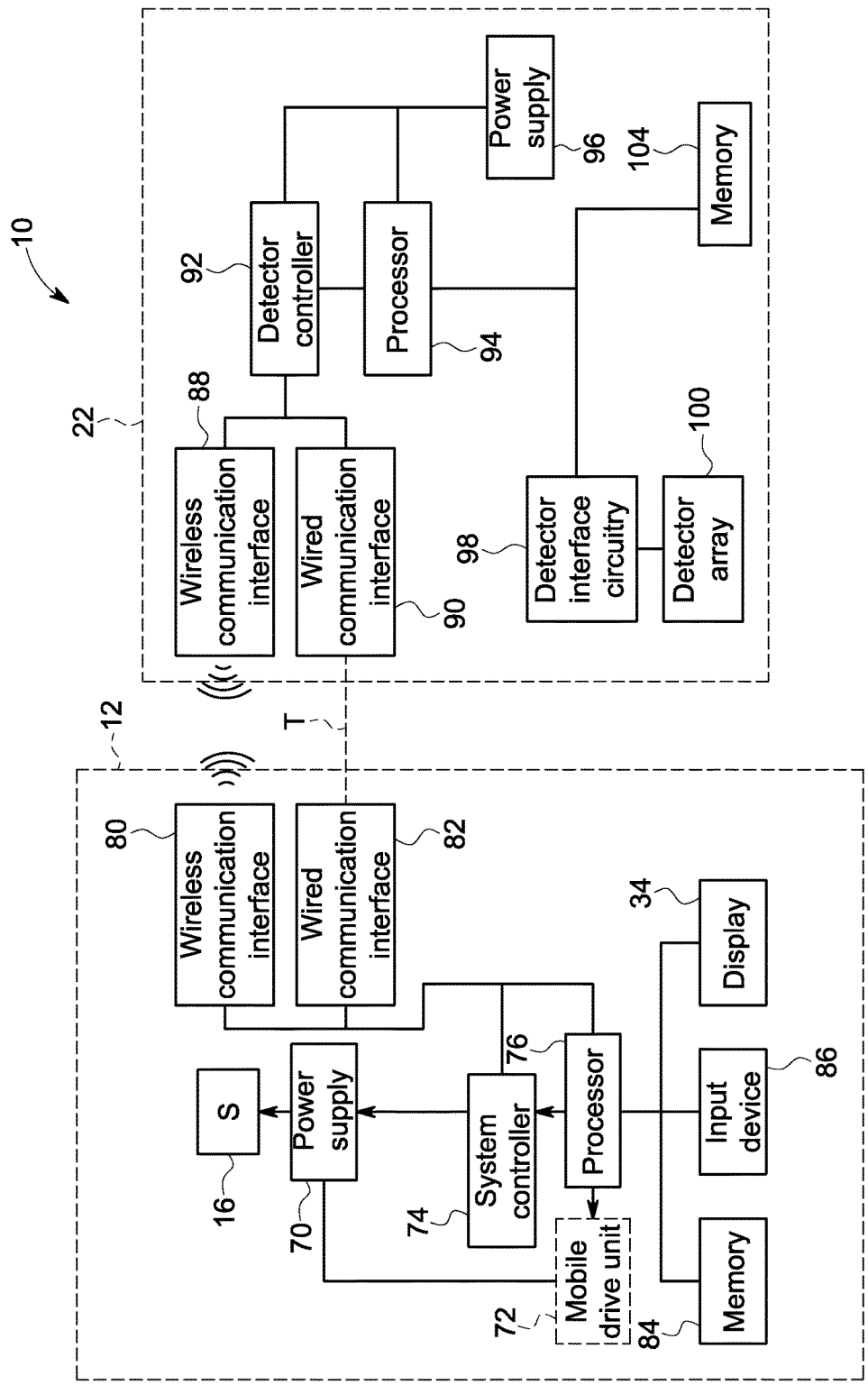
FIG. 3 is a diagrammatical overview of an embodiment of an X-ray system.

Regardless of the differences between the X-ray systems 10 shown in FIGS. 1 and 2, certain features internal to the X-ray system 10 remain consistent across different embodiments. These components are illustrated diagrammatically in FIG. 3. The imager system 12 includes the X-ray source 16 of radiation. The X-ray source 16 is controlled by a power supply 70, which furnishes both power and control signals for examination sequences. In addition, in mobile imaging systems the power supply 70 furnishes power to a mobile drive unit 72 of the wheeled base 58. The power supply 70 is responsive to signals from a system controller 74. In general, the system controller 74 commands operation of the imaging system to execute examination protocols and to process acquired image data. In the present context, the system controller 74 also includes signal processing circuitry, typically based upon a general purpose or application-specific digital computer, associated memory circuitry for storing programs and routines executed by the computer, as well as configuration parameters and image data, interface circuits, and so forth. The system controller 74 may include or may be responsive to a processor 76. The processor 76 receives image data from the detector 22 and processes the data to reconstruct an image of a subject.

The processor 76 is linked to a wireless communication interface 80 that allows wireless communication with the detector 22. Further, the processor 76 is linked to a wired communication interface 82 that allows communication with the detector 22 via a tether (e.g., a multi-conductor cable). The imager system 12 may also be in communication with a server. The processor 76 is also linked to a memory 84, an input device 86, and the display 34. The memory 84 stores configuration parameters, calibration files received from the detector 22, and lookup tables used for image data processing. The input device 86 may include a mouse, keyboard, or any other device for receiving user input, as well as to acquire images using the imager system 12. The display 34 allows visualization of output system parameters, images, and so forth.

The detector 22 includes a wireless communication interface 88 for wireless communication with the imager system 12, as well as a wired communication interface 90, for communicating with the detector 22 when it is tethered to the imager system 12. The detector 22 may also be in communication with a server. It is noted that the wireless communication interface 88 may utilize any suitable wireless communication protocol, such as an ultra wideband (UWB) communication standard, a Bluetooth communication standard, or any 802.11 communication standard. Moreover, the detector 22 is coupled to a detector controller 92 which coordinates the control of the various detector functions. For example, the detector controller 92 may execute various signal processing and filtration functions, such as for initial adjustment of dynamic ranges, interleaving of digital image data, and so forth. The detector controller 92 is responsive to signals from the system controller 74, as well as the detection circuitry 78. The detector controller 92 is linked to a processor 94. The processor 94, the detector controller 92, and all of the circuitry receive power from a power supply 96. The power supply 96 may include a battery. In some embodiments, the detector 22, including the power supply 96, may receive power from the power supply 70 when tethered to the imager system 12.

Also, the processor 94 is linked to detector interface circuitry 98. The detector 22, which again may be used in radiographic or fluoroscopic imaging systems, converts X-ray photons received on its surface to lower energy photons. The detector 22 includes a detector array 100 that includes an array of photodetector elements to convert the light photons to electrical signals, which are representative of the number of photons or the intensity of radiation impacting individual pixel regions of the detector surface. Alternatively, the detector 22 may convert the X-ray photons directly to electrical signals. These electrical signals are converted to digital values by the detector interface circuitry 98, which provides the values to the processor 94 to be converted to imaging data and sent to the imager system 12 to reconstruct an image of the features within a subject. Alternatively, the imaging data may be sent from the detector 22 to a server to process the imaging data. In a present form, the detector array 100 is formed of silicon complimentary metal-oxide-semiconductors (CMOS). The array elements, or receptors, are organized in rows and columns, with each receptor consisting of a photodiode and complementary and symmetrical pairs of p-type and metal oxide semiconductor field effect transistors (MOSFET). The cathode of each diode is connected to the source of the transistor, and the anodes of all diodes are connected to a negative bias voltage. The gates of the transistors in each row are connected together and the row electrodes are connected to scanning electronics. The drains of the transistors in a column are connected together and the electrode of each column is connected to an individual data channel of the detector interface circuitry 98.

Further, the processor 94 is linked to a memory 104. The memory 104 may store various configuration parameters, calibration files, and detector identification data. In addition, the memory 104 may store slope maps used to determine a pixel correction applied to the image data collected by the detector 22. These slope maps may be generated based on calculations discussed in detail below. In some embodiments, these slope maps may be determined via the processor 76 and stored in the memory 84 of the imager system 12, and not the detector 22 itself. That is, either the imager system 12 or the detector 22 may store and process the calibration data collected by the detector 22.

Each receptor of the detector array 100 may output a different signal value to the processor 94 in response to receiving a certain dose of radiation. That is, the relationship between X-ray dose and receptor output may be different for each receptor. In order for the signals received from each of the receptors to form an accurate X-ray image, the detector 22 may first be calibrated to determine a gain correction to apply to X-ray image data that is later collected using the detector 22. In present embodiments, the dynamic range of the detector 22 is relatively small, such that the detector 22 uses the entire available dynamic range. As a result, there may be inherent non-linearity in the relationship between X-ray dose and receptor output for any given receptor. As a result, the pixel value of any pixel within the detector array 100 may vary nonlinearly with respect to the X-ray dose applied to the pixel. Calibrating such a detector 22 at a single X-ray dose of radiation may yield a gain correction map that, when applied to other X-ray image data sets, would introduce shape artifacts into the corrected X-ray image. To reduce these artifacts, the detector 22 may be configured to perform a separate calibration across multiple pixel value regions within the receptor's dynamic range.

Figure 4:
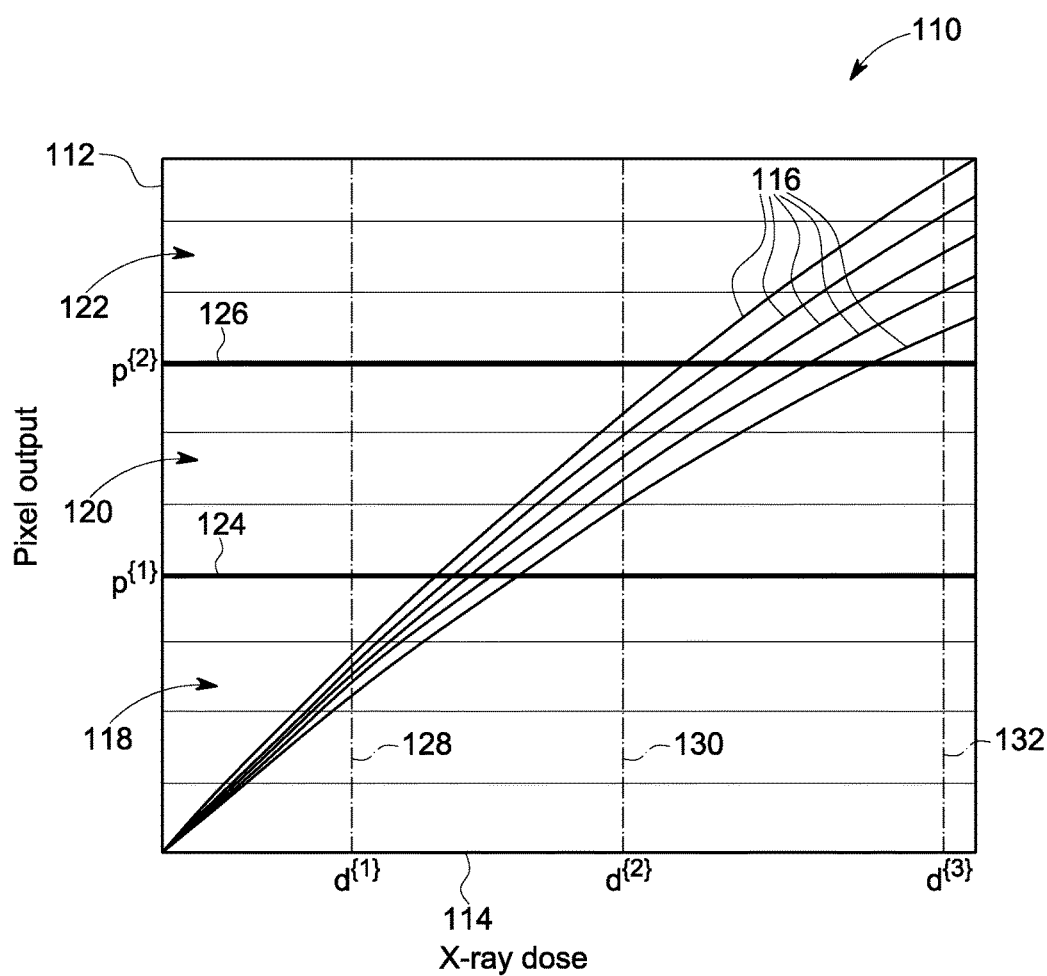
FIG. 4 is a plot illustrating an embodiment of pixel output versus X-ray dose.

To demonstrate this method of calibration, FIG. 4 is a plot 110 illustrating an embodiment of pixel output 112 versus X-ray dose 114. The pixel output 112 is related to the signal generated by a pixel of the detector array 100 when a certain dose 114 of radiation is applied to the detector 22. Five traces 116 shown on the plot 110 are representative of five pixels, located at various spatial locations within the detector array 100. The illustrated traces 116 show a nonlinear relationship between pixel output 112 and X-ray dose 114 for each of their respective pixels of the detector array 100.

To account for such nonlinearity during image correction, the plot 110 shows the pixel output 112 divided into sections, or pixel value regions. Each pixel value region has a different range of pixel values. In the illustrated embodiment, the pixel output 112 is divided into three pixel value regions 118, 120, and 122. The pixel output 112 may be divided into any number of different pixel value regions, depending on the relationship of the pixel output 112 to the X-ray dose 114, acceptable calibration error, and other factors. The pixel value regions 118, 120, and 122 each have at least one pixel value boundary separating values of the pixels within a respective pixel value region from pixels values within another pixel value region. For example, in the illustrated plot 110, a pixel value boundary 124 indicates the dividing line between the pixel value regions 118 and 120. Similarly, another pixel value boundary 126 divides the pixel value regions 120 and 122. Because there are two pixel value boundaries 124 and 126, the illustrated pixel gain model is bilinear. It should be noted that the pixel value boundaries 124 and 126 are the same for each pixel in the detector array 100. The first pixel value region 118 includes all pixel outputs 112 between 0 and $p^{\{1\}}$ (e.g., 124), the second pixel value region 120 includes all pixel outputs 112 between $p^{\{1\}}$ (e.g., 124) and $p^{\{2\}}$ (e.g., 126), and the third pixel value region 122 includes all pixel outputs 112 above the value of $p^{\{2\}}$ (e.g., 126). The processor 94 may determine the appropriate pixel value boundaries 124 and 126, e.g., based on the available dynamic range of the detector array 100, by implementing machine-readable code stored in the memory 104. In certain embodiments, a user may select the pixel value boundaries 124 and 126 via the input device 86, and the processor 94 may receive and determine the division of pixel values based on this user selection. It should be noted that there may be any number of pixel value boundaries selected in order to divide the pixels of X-ray image data into a desired number of pixel value regions for calibration and correction of X-ray image data.

Once the pixel output 112 is divided into a number of pixel value regions having different ranges of pixel values, an image calibration may be performed for each pixel value region. The calibration may include applying a certain dose 114 of radiation to the detector 22 and storing the resulting pixel outputs 112 from each pixel of the detector array 100. The illustrated plot 110 shows three different doses 128, 130, and 132 of radiation applied to the pixel value regions 118, 120, and 122, respectively. These doses 128, 130, and 132 may be selected such that the pixel output 112 for the different pixels at each dose are substantially central within the range of pixel values for the respective pixel value region. To reduce noise, multiple images may be acquired at each of the doses 128, 130, and 132, and the images may be averaged together to create gain maps for each of the pixel value regions 118, 120, and 122, as discussed in detail below. In some embodiments, the X-ray system 10 may be used to determine each of the doses 128, 130, and 132 of radiation, apply the doses 128, 130, and 132, acquire the pixel outputs 112 at each dose, and select the pixel value boundaries 124 and 126 based on the pixel outputs 112.

From the pixel outputs 112 collected in response to applying each dose of radiation to the detector array 100, an average gain calibration image may be determined for each dose. The calibration image includes the pixel output 112 of each detector pixel in response to a certain radiation dose. Multiple calibration images may be collected for the same X-ray dose, and the image data for each calibration image averaged together to yield the average calibration image. For a detector 22 divided into three pixel value regions 118, 120, and 122, as shown in the illustrated embodiment, the average calibration image for each respective region may be denoted as $\{p_{i,j}^{\{1\}}\}$, $\{p_{i,j}^{\{2\}}\}$, and $\{p_{i,j}^{\{3\}}\}$.

Figure 5:
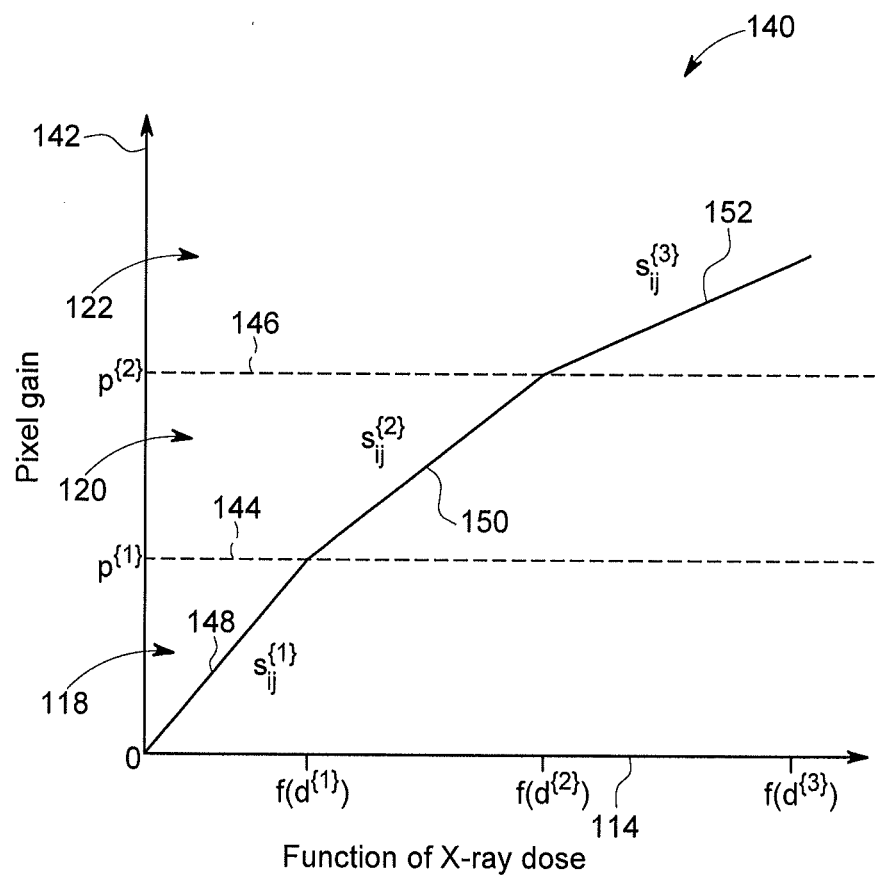
FIG. 5 is a plot illustrating an embodiment of pixel gain correction versus X-ray dose.

FIG. 5 is a plot 140 illustrating an embodiment of pixel gain correction 142 as a function of X-ray dose 114. The pixel gain correction 142, once determined, may be applied to X-ray image data collected by the detector 22, in order to reduce any image artifact caused by nonlinearity in the X-ray pixels or detector elements. In this way, the pixel gain correction 142 relates to the pixel outputs 112 discussed with respect to FIG. 4. The pixel gain correction 142 is applied in three linear sections in the illustrated embodiment, representing the same three pixel value regions 118, 120, and 122 of FIG. 4. These pixel value regions 118, 120, and 122 are separated by pixel gain value boundaries 144 and 146, which are the pixel gain values corresponding to the pixel value boundaries 124 and 126, respectively. In calibrating the detector 22, the average pixel gain correction 142 is determined for each of the doses 128, 130, and 132 of radiation applied to the detector 22. Again, these doses 128, 130, and 132 correspond with pixel outputs 112 relatively central to the pixel value regions 118, 120, and 122. As discussed in detail below, the processor 94 of the detector 22 may determine gain slopes 148, 150, and 152 of the pixel correction 142 for the respective pixel value regions 118, 120, and 122. These gain slopes 148, 150, and 152 may be respectively referred to as $s_{i,j}^{\{1\}}$, $s_{i,j}^{\{2\}}$, and $s_{i,j}^{\{3\}}$. In certain embodiments, the gain slopes 148, 150, and 152 may be determined according to the following equations:

$$s_{i,j}^{\{1\}} = \frac{\alpha \times \text{median}\{p_{i,j}^{\{1\}}\}}{p_{i,j}^{\{1\}}}, \quad (1)$$

$$s_{i,j}^{\{2\}} = \frac{\alpha \times \text{median}\{p_{i,j}^{\{2\}} - p^{\{1\}}\}}{p_{i,j}^{\{2\}} - p^{\{1\}}}, \text{ and} \quad (2)$$

$$s_{i,j}^{\{3\}} = \frac{\alpha \times \text{median}\{p_{i,j}^{\{3\}} - p^{\{2\}}\}}{p_{i,j}^{\{3\}} - p^{\{2\}}}. \quad (3)$$

In the first equation, used to calculate the gain slope of the first pixel value region 118, median $\{p_{i,j}^{\{1\}}\}$ represents a median of the average gain calibration image for the first pixel value region 118. This may be determined by generating calibration images at one or more X-ray doses 114 yielding pixel outputs 112 within the first pixel value region 118. Again, such calibration images may themselves be an average image taken from a number of calibration images generated using the same dose 114 of radiation. The pixel value $p_{i,j}^{\{1\}}$ represents the pixel output 112 corresponding with the median of the average gain calibration image. For example, if one dose (e.g., 128) of radiation is applied for the first pixel value region 118, $p_{i,j}^{\{1\}}$ would be the average pixel output of a pixel at a certain location, and median $\{p_{i,j}^{\{1\}}\}$ would be the average gain calibration image at the location. Since a lower pixel value boundary of the first pixel value region 118 is 0, both median $\{p_{i,j}^{\{1\}}\}$ and $p_{i,j}^{\{1\}}$ are relative values in Equation (1). Similarly, median $\{p_{i,j}^{\{2\}}-p_{\{1\}}\}$ and $p_{i,j}^{\{2\}}-p^{\{1\}}$ are relative with respect to the lower pixel value boundary 124 of the second pixel value region 120. Likewise, median $\{p_{i,j}^{\{3\}}-p^{\{2\}}\}$ and $p_{i,j}^{\{3\}}-p^{\{2\}}$ are relative with respect to the lower pixel value boundary 126 of the third pixel value region 122.

In the equations shown above, α represents a scaling factor applied to the gain slope calculations. The scaling factor α may be determined such that a maximum pixel value of the gain corrected image is near a desired maximum count level when a maximum dose 114 of radiation is applied to the detector 22. The desired maximum count level may be an upper pixel value limit based on an available bit-width of the image data. For example, the pixel values may vary from 0 to 16383 in a system that generates 14-bit digital image data. Thus, the scaling factor α may be calculated by the processor 94 such that the upper pixel value limit (e.g., 16383) corresponds to the gain corrected pixel value for a pixel receiving the maximum available X-ray dose 114 used in the X-ray system 10. This enables the corrected X-ray image data to span a full range of available digital pixel values.

The gain slopes 148, 150, and 152 may be calculated from the average calibration images associated with the pixel value regions 118, 120, and 122. Once calculated, the gain slopes 148, 150, and 152 may be used to determine the pixel gain correction 142 to be applied to image data at any X-ray dose 114. For example, the gain slope 148 may be used to interpolate an appropriate gain correction 142 for any pixel of image data that is within the first pixel value region 118. In an embodiment having three pixel value regions 118, 120, and 122, such as FIG. 6, the pixel gain correction may be calculated by the processor 94 according to the following equations:

$$\hat{p}_{i,j} = \begin{cases} p_{i,j} \times s_{i,j}^{\{1\}}, & \text{if } p_{i,j} \leq p^{\{1\}} \quad (4) \\ p^{\{1\}} \times s_{i,j}^{\{1\}} + (p_{i,j} - p^{\{1\}}) \times s_{i,j}^{\{2\}}, & \text{if } p^{\{1\}} < p_{i,j} \leq p^{\{2\}}(5) \\ p^{\{1\}} \times s_{i,j}^{\{1\}} + (p^{\{2\}} - p^{\{1\}}) \times s_{i,j}^{\{2\}} + (p_{i,j} - p^{\{2\}}) \times s_{i,j}^{\{3\}}, & \text{if } p^{\{2\}} < p_{i,j}. \quad (6) \end{cases}$$

In the above equations, $p_{i,j}$ represents a pixel output measured at the i, j position of the detector array 100. After determining the appropriate gain correction 142 for a pixel based on the pixel output 112, the gain correction 142 may be applied to the pixel to reduce artifacts in the image data caused by detector nonlinearity. In some embodiments, the gain correction 142 may be a value subtracted from the X-ray image data collected for each of the pixels on the detector array 100. However, other embodiments of the detector 22 may apply the gain correction 142 in different ways to generate corrected X-ray image data based on the gain slope maps.

Figure 6:
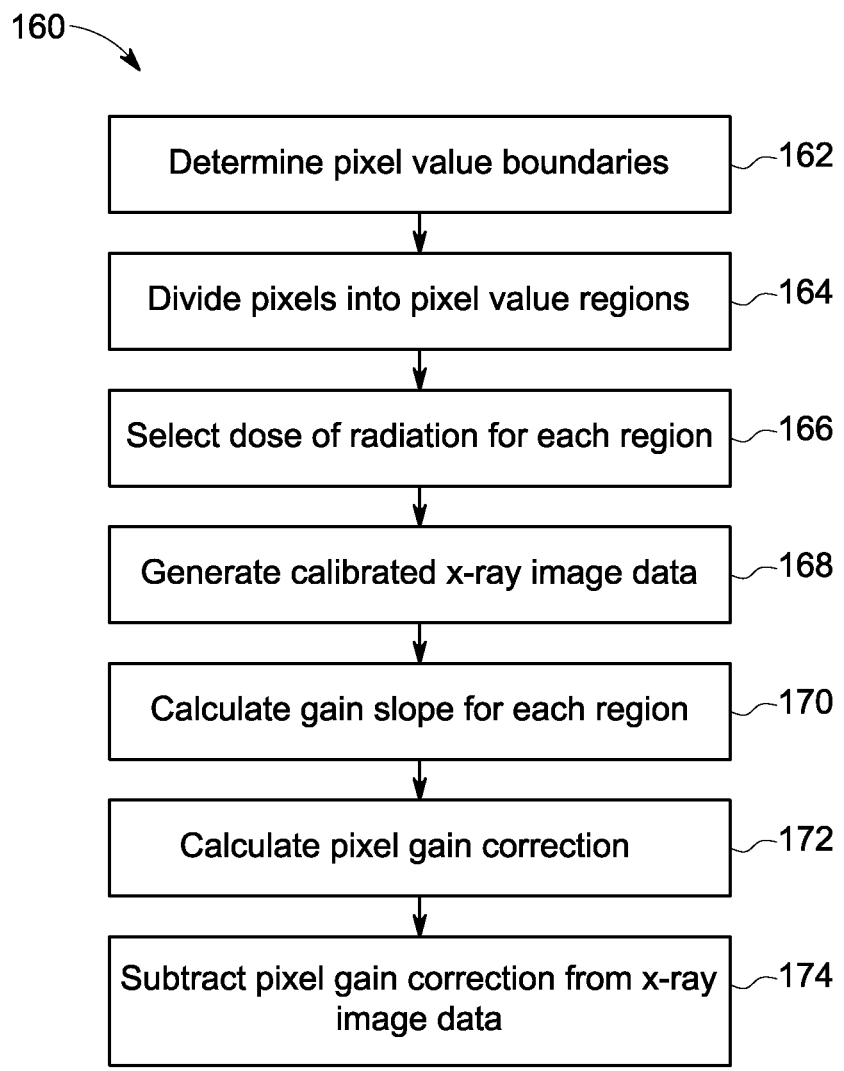
FIG. 6 is a process flow diagram of an embodiment of a method for correcting for image artifacts in an X-ray system.

FIG. 6 is a process flow diagram of a method 160 for correcting for image artifacts in the X-ray system 10. It should be noted that the method 160 may be a computer-implemented method performed via one or more processor-executable routines encoded on one or more non-transitory computer-readable media (e.g., memory 104). When executed by the processor 94, these routines cause the acts shown in the method 160 to be performed. Specifically, this method 160 enables the processor 94 (i.e., processing circuitry) to generate multiple slope maps used to apply a gain correction to the X-ray image data collected after calibration of the detector 22. The term non-transitory merely indicates that the medium is not a signal.

The method 160 includes determining (block 162) pixel value boundaries (e.g., 124, 126) of pixel value regions (e.g., 118, 120, 122) of the pixel output 112, and dividing (block 164) the pixels of the X-ray image data into at least two pixel value regions (e.g., 118, 120, 122). As previously discussed, each pixel value region has a different range of pixel values, and the pixels of X-ray image data are divided based on the value of each pixel. The pixel value boundaries separate the values of pixels in each of the pixel value regions, and these boundaries may be determined based on a user selection. The method 160 may include selecting (block 166) the dose (e.g., 128, 130, 132) of radiation for each pixel value region (e.g., 118, 120, 122) such that a receptor output at each radiation dose is substantially central within the respective pixel value region. The method 160 further includes generating (block 168) calibrated X-ray image data for each pixel value region (e.g., 118, 120, 122). This may refer to generating one or more average calibration images for each pixel value region, where every calibration image is generated using a different dose 114 of radiation.

The method 160 includes calculating (block 170) a gain slope (e.g., 148, 150, 152) for each pixel value region (e.g., 118, 120, 122) based on the calibrated X-ray image data. An example of one such calculation is given above in Equations (1)-(3), and is described with reference to FIG. 7 below. However, other calculations may be possible for determining the gain slopes. The method 160 also includes calculating (block 172) a pixel gain correction 142 for the pixels of the X-ray image data based on at least one of the calculated gain slopes (e.g., 148, 150, 152). The details of one such calculation are given in Equations (4)-(6) above and described with reference to FIG. 8 below. In addition, the method 160 may include subtracting (block 174) the pixel gain correction from X-ray image data collected by the detector 22 to generate a corrected X-ray image. The detector 22 may communicate the corrected X-ray image to the imager system 12 of the X-ray system 10 for storage in the memory 84 or visualization on the display 34.

Figure 7:
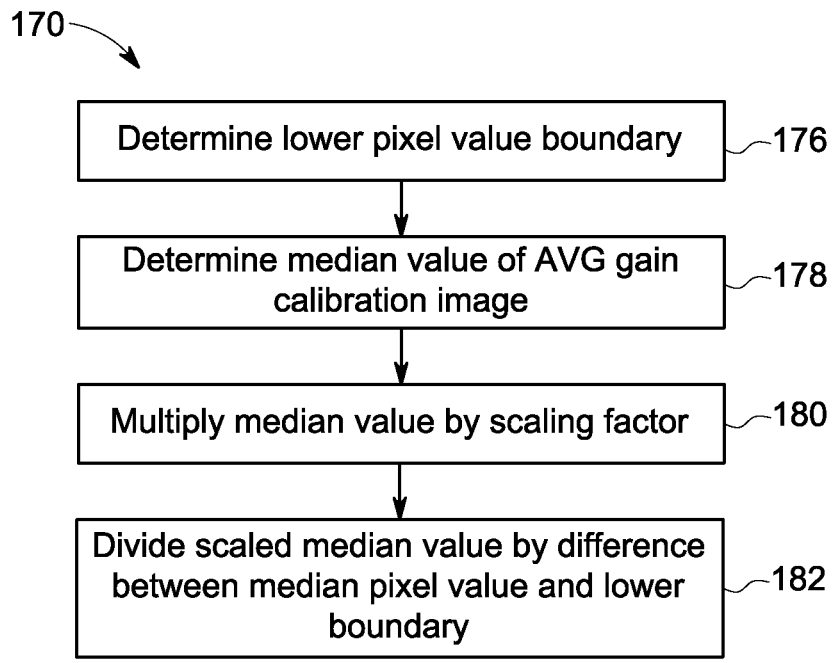
FIG. 7 is a process flow diagram of an embodiment of a method for calculating a gain slope for a pixel value region.

FIG. 7 is a process flow diagram of a method for calculating (block 170) the gain slope (e.g., 148, 150, 152) for a pixel value region (e.g., 118, 120, 122). This includes determining (block 176) a lower pixel value boundary (e.g., 0, $p^{\{1\}}$, $p^{\{2\}}$) for the pixel value region. The method also includes determining (block 178) the median value of the average gain calibration image (e.g., $\{p_{i,j}^{\{1\}}\}$, $\{p_{i,j}^{\{2\}}\}$, $\{p_{i,j}^{\{3\}}\}$) for the respective pixel value region. The method further includes multiplying (block 180) the median value by a scaling factor (e.g., α) to generate a scaled median value, and dividing (block 182) the scaled median value by a difference between a median pixel value (e.g., $p_{i,j}^{\{1\}}$, $p_{i,j}^{\{2\}}$, $p_{i,j}^{\{3\}}$), which corresponds with the median value of the average gain calibration image, and the lower pixel value boundary. This method represents the calculation performed in Equations (1)-(3) above, and may be used to determine the gain slope for each pixel value region.

Figure 8:
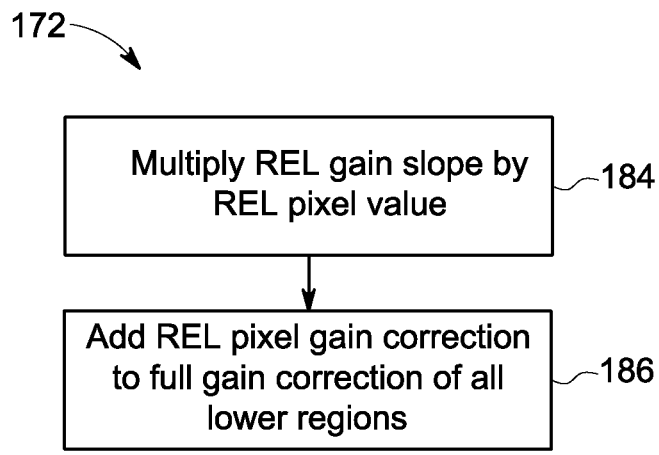
FIG. 8 is a process flow diagram of an embodiment of a method for calculating a pixel gain correction.

FIG. 8 is a process flow diagram of a method for calculating (block 172) the pixel gain correction (e.g., $\hat{p}_{i,j}$) for a pixel based on its measured pixel output 112 and the pixel value region (e.g., 118, 120, 122) that contains this pixel output 112. This method includes multiplying (block 184) the gain slope (e.g., 148, 150, 152) of the respective pixel value region by a relative pixel value to determine a relative pixel gain correction. This relative pixel value refers to the measured pixel value (e.g., $p_{i,j}$) minus the lower pixel value boundary (e.g., 0, $p^{\{1\}}$, $p^{\{2\}}$) of the pixel value region. The method also includes adding (block 186) the relative pixel gain correction to a full pixel gain correction of all other pixel value regions with pixel values below the lower pixel value boundary. For example, since there are no pixel value regions having lower pixel values than the first pixel value region 118, the relative pixel gain correction $p_{i,j} \times s_{i,j}^{\{1\}}$ is the pixel gain correction, as shown in Equation (4). In the second pixel value region 120, however, the relative pixel gain correction $(p_{i,j}-p^{\{1\}}) \times s_{i,j}^{\{2\}}$ is added to the full pixel value correction $p^{\{1\}} \times s_{i,j}^{\{1\}}$ of the first pixel value region 118, as shown in Equation (5). Similarly, in the third pixel value region 122, the relative pixel gain correction $(p_{i,j}-p^{\{2\}}) \times s_{i,j}^{\{3\}}$ is added to the full pixel value correction $p^{\{1\}} \times s_{i,j}^{\{1\}}$ of the first pixel value region 118 and the full pixel value correction $(p^{\{2\}}-p^{\{1\}}) \times s_{i,j}^{\{2\}}$ of the second pixel value region 120, as shown in Equation (6). Other calculations may be performed to determine a pixel gain correction to be applied for any of the pixel value regions 118, 120, and 122 based on at least the gain slopes determined from the multiple calibration images taken at different doses of radiation.

Technical effects of the disclosed embodiments include, among other things, a method of calibrating a digital X-ray detector (used in radiographic or fluoroscopic X-ray imaging systems) that makes full use of a relatively small dynamic range. This would result in image data artifacts in X-ray systems that determine gain corrections using a one-part linear calibration scheme. Instead, present embodiments provide a gain correction that reduces such artifacts based on simple calculations performed for a number (two or more) of different pixel value regions. By dividing the pixel outputs of the detector array into multiple pixel value regions, each pixel value region may be calibrated separately to determine a gain slope representative of the average gain calibration image for that particular range of pixel values. After this calibration is performed for each region, the gain correction may be determined according to a simple equation based on the gain slopes and pixel outputs of the detector array. This may allow for relatively simple calibration and correction of X-ray image data collected via receptors with nonlinear relationships between X-ray dose and pixel output. Since the level of calibration is defined based on the pixel output of the receptor, the image correction is relatively straightforward to implement. The calculations are linear, making them computationally simple for the processor to apply across all pixels of the detector array. This may save image processing time while extending the use of the detector's dynamic range.

This written description uses examples to disclose present embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for reducing image artifacts in X-ray image data, comprising:
   dividing pixels of X-ray image data into a plurality of pixel value regions based on a pixel value of each pixel, wherein each pixel value region has a different range of pixel values;
   generating calibrated X-ray image data for each pixel value region, wherein the respective calibrated X-ray image data for each pixel value region is generated from image data acquired during exposure to a different dose of radiation;
   calculating a gain slope for each pixel value region based on the calibrated X-ray image data; and
   calculating a pixel gain correction for the pixels of the X-ray image data based on at least one of the calculated gain slopes.

2. The method of claim 1, wherein each of the pixel value regions has at least one pixel value boundary separating values of pixels within the respective pixel value region from other values of pixels within another pixel value region.

3. The method of claim 2, wherein dividing the pixels of X-ray image data comprises determining the pixel value boundaries based on a user selection.

4. The method of claim 1, comprising selecting the dose of radiation for each pixel value region such that a receptor output at each radiation dose is substantially central within the respective pixel value region.

5. The method of claim 4, wherein generating the calibrated X-ray image data comprises:
   acquiring a plurality of images from a digital X-ray detector for each selected dose of radiation; and
   averaging the plurality of images acquired at each selected dose to determine an average gain calibration image for each pixel value region.

6. The method of claim 1, wherein calculating the pixel gain correction comprises:
   multiplying the gain slope by a relative pixel value to determine a relative pixel gain correction, wherein the relative pixel value is a pixel value within the respective pixel value region minus a lower pixel value boundary of the respective pixel value region; and
   adding the relative pixel gain correction to a full pixel gain correction of all other pixel value regions having pixel values below the lower pixel value boundary.

7. The method of claim 1, comprising subtracting the pixel gain correction from X-ray image data collected using a digital X-ray detector to generate a corrected X-ray image.

8. One or more non-transitory computer-readable media encoding one or more processor-executable routines, wherein the one or more routines, when executed by a processor, cause acts to be performed, comprising:
   dividing pixels of X-ray image data into a plurality of pixel value regions based on a pixel value of each pixel, wherein each pixel value region has a different range of pixel values;
   generating calibrated X-ray image data for each pixel value region, wherein the respective calibrated X-ray image data for each pixel value region is generated from image data acquired during exposure to a different dose of radiation;

calculating a gain slope for each pixel value region based on the calibrated X-ray image data; and calculating a pixel gain correction for the pixels of the X-ray image data based on at least one of the calculated gain slopes.

9. The one or more non-transitory computer-readable media of claim 8, wherein the one or more routines, when executed by the processor, cause further acts to be performed comprising:

determining a pixel value boundary based on a user selection, wherein the pixel value boundary separates values of pixels within the respective pixel value region from other values of pixels within another pixel value region.

10. The one or more non-transitory computer-readable media of claim 8, wherein the one or more routines, when executed by the processor, cause further acts to be performed comprising:

selecting the dose of radiation for each pixel value region such that a receptor output at each radiation dose is substantially central within the respective pixel value region.

11. The one or more non-transitory computer-readable media of claim 10, wherein the one or more routines, when executed by the processor, cause further acts to be performed comprising:

acquiring a plurality of images from a digital X-ray detector for each selected dose of radiation; and averaging the plurality of images acquired at each selected dose to determine an average gain calibration image for each pixel value region.

12. The one or more non-transitory computer-readable media of claim 8, wherein the one or more routines, when executed by the processor, cause further acts to be performed comprising:

multiplying the gain slope by a relative pixel value to determine a relative pixel gain correction, wherein the relative pixel value is a pixel value within the respective pixel value region minus a lower pixel value boundary of the respective pixel value region; and adding the relative pixel gain correction to a full pixel gain correction of all other pixel value regions having pixel values below the lower pixel value boundary to generate the pixel gain correction.

13. The one or more non-transitory computer-readable media of claim 8, wherein the one or more routines, when executed by the processor, cause further acts to be performed comprising:

subtracting the pixel gain correction from X-ray image data collected using a digital X-ray detector to generated a corrected X-ray image.

14. An imaging system, comprising:

a radiation source;

a digital X-ray detector configured to generate X-ray image data;

control circuitry configured to acquire the X-ray image data from the digital X-ray detector; and processing circuitry configured to apply a gain correction to the X-ray image data via a plurality of slope maps, wherein the processing circuitry is configured to generate the slope maps by executing code to perform the acts of:

dividing pixels of X-ray image data into a plurality of pixel value regions based on a pixel value of each pixel, wherein each pixel value region has a different range of pixel values;

generating calibrated X-ray image data for each pixel value region, wherein the respective calibrated X-ray image data for each pixel value region is generated from image data acquired during exposure to a different dose of radiation; and calculating a gain slope for each pixel value region based on the calibrated X-ray image data.

15. The imaging system of claim 14, wherein the processing circuitry is configured to apply the gain correction based on at least one of the calculated gain slopes.

16. The imaging system of claim 14, wherein the digital X-ray detector comprises a complementary metal-oxide-semiconductor (CMOS) based detector.

17. The imaging system of claim 14, wherein the processing circuitry is configured to generate the slope maps by executing code to perform the further acts of:

determining a pixel value boundary based on a user selection, wherein the pixel value boundary separates values of pixels within the respective pixel value region from other values of pixels within another pixel value region.

18. The imaging system of claim 14, wherein the processing circuitry is configured to generate the slope maps by executing code to perform the further acts of:

selecting the dose of radiation for each pixel value region such that a receptor output at each radiation dose is substantially central within the respective pixel value region.

19. The imaging system of claim 14, wherein the processing circuitry is configured to generate the slope maps by executing code to perform the further acts of:

acquiring a plurality of images from the digital X-ray detector for each selected dose of radiation; and averaging the plurality of images acquired at each selected dose to determine an average gain calibration image for each pixel value region.

20. The imaging system of claim 14, wherein the processing circuitry is configured to generate the slope maps by executing code to perform the further acts of:

multiplying the gain slope by a relative pixel value to determine a relative pixel gain correction, wherein the relative pixel value is a pixel value within the respective pixel value region minus a lower pixel value boundary of the respective pixel value region; and adding the relative pixel gain correction to a full pixel gain correction of all other pixel value regions having pixel values below the lower pixel value boundary to generate the gain correction.

21. The imaging system of claim 14, wherein the processing circuitry is configured to apply the gain correction by subtracting the gain correction from X-ray image data collected using the digital X-ray detector to generate a corrected X-ray image.

* * * * *